(12) United States Patent
Babico

(10) Patent No.: US 11,116,984 B2
(45) Date of Patent: Sep. 14, 2021

(54) EXTENDED LENGTH ANTENNA ASSEMBLY FOR USE WITHIN A MULTI-COMPONENT SYSTEM

(71) Applicant: Advanced Bionics AG, Staefa (CH)

(72) Inventor: John Y. Babico, Tucson, AZ (US)

(73) Assignee: Advanced Bionics AG, Staefa (CH)

( * ) Notice: Subject to any disclaimer, the term of this patent is extended or adjusted under 35 U.S.C. 154(b) by 369 days.

(21) Appl. No.: 16/120,196

(22) Filed: Aug. 31, 2018

(65) Prior Publication Data

US 2019/0076662 A1    Mar. 14, 2019

Related U.S. Application Data

(60) Provisional application No. 62/556,265, filed on Sep. 8, 2017.

(51) Int. Cl.
    *A61N 1/372*    (2006.01)
    *H05K 1/14*    (2006.01)
    (Continued)

(52) U.S. Cl.
    CPC ..... *A61N 1/37229* (2013.01); *A61N 1/36038* (2017.08); *A61N 1/37217* (2013.01); *A61N 1/37223* (2013.01); *H01Q 1/273* (2013.01); *H01Q 7/00* (2013.01); *H04R 25/554* (2013.01); *H04R 25/602* (2013.01); *H04R 25/65* (2013.01); *H05K 1/118* (2013.01); *H05K 1/147* (2013.01); *H05K 1/189* (2013.01); *A61N 1/0541* (2013.01); *H01Q 9/26* (2013.01); *H04R 25/552* (2013.01); *H04R 2225/51* (2013.01);
    (Continued)

(58) Field of Classification Search
    CPC ............ A61N 1/37229; A61N 1/36038; A61N 1/0541; H01Q 1/273; H01Q 7/00; H01Q 9/26; H01Q 9/265; H01Q 1/44; H01K 1/189
    See application file for complete search history.

(56) References Cited

U.S. PATENT DOCUMENTS 6,067,474 A * 5/2000 Schulman ......... H01M 10/0436
                                                     607/57
7,530,823 B1 * 5/2009 Thornton ............. H01Q 1/2275
                                                     439/131
(Continued)

*Primary Examiner* — Eric D. Bertram
(74) *Attorney, Agent, or Firm* — ALG Intellectual Property, LLC

(57) ABSTRACT

A multi-component system includes a first component housing a first conductive pad, a second conductive pad, and a first portion of a loop antenna that terminates on one side at the first conductive pad and on another side at the second conductive pad. The multi-component system further includes a second component housing a third conductive pad, a fourth conductive pad, and a second portion of the loop antenna that terminates on one side at the third conductive pad and on another side at the fourth conductive pad. The second component is distinct from, and configured to detachably couple with, the first component such that the first and third conductive pads, and the second and fourth conductive pads, respectively form first and second non-galvanic couplings that capacitively couple the first and second portions of the loop antenna while the first and second portions of the loop antenna remain galvanically separated.

28 Claims, 9 Drawing Sheets

(51) Int. Cl.
*H05K 1/18* (2006.01)
*A61N 1/36* (2006.01)
*H01Q 7/00* (2006.01)
*H01Q 1/27* (2006.01)
*H04R 25/00* (2006.01)
*H05K 1/11* (2006.01)
*A61N 1/05* (2006.01)
*H01Q 9/26* (2006.01)

(52) U.S. Cl.
CPC .................. *H04R 2225/67* (2013.01); *H05K 2201/10015* (2013.01); *H05K 2201/10037* (2013.01); *H05K 2201/10083* (2013.01)

(56) References Cited

U.S. PATENT DOCUMENTS

| | | | |
|---|---|---|---|
| 7,724,196 B2 | 5/2010 | Kinezos et al. | |
| 8,193,998 B2 | 6/2012 | Puente Baliarda et al. | |
| 8,730,121 B2 * | 5/2014 | Jiang | H01Q 11/14 343/803 |
| 9,295,848 B2 * | 3/2016 | Meskens | A61N 1/37229 |
| 9,431,700 B2 | 8/2016 | Desclos et al. | |
| 9,609,443 B2 | 3/2017 | Ruaro et al. | |
| 2008/0303633 A1 | 12/2008 | Cheng et al. | |
| 2009/0228074 A1 * | 9/2009 | Edgell | H01Q 1/36 607/60 |
| 2009/0243953 A1 * | 10/2009 | Keilman | H01Q 1/273 343/793 |
| 2010/0176993 A1 | 7/2010 | Pedersen | |
| 2012/0130206 A1 * | 5/2012 | Vajha | A61B 5/0031 600/302 |
| 2013/0113666 A1 * | 5/2013 | Orsi | H01Q 5/35 343/745 |
| 2015/0022402 A1 * | 1/2015 | Gavilan | H01Q 7/00 343/702 |
| 2015/0296312 A1 | 10/2015 | Nikles et al. | |
| 2016/0337766 A1 | 11/2016 | Flaig | |
| 2016/0381471 A1 | 12/2016 | Henriksen et al. | |

* cited by examiner

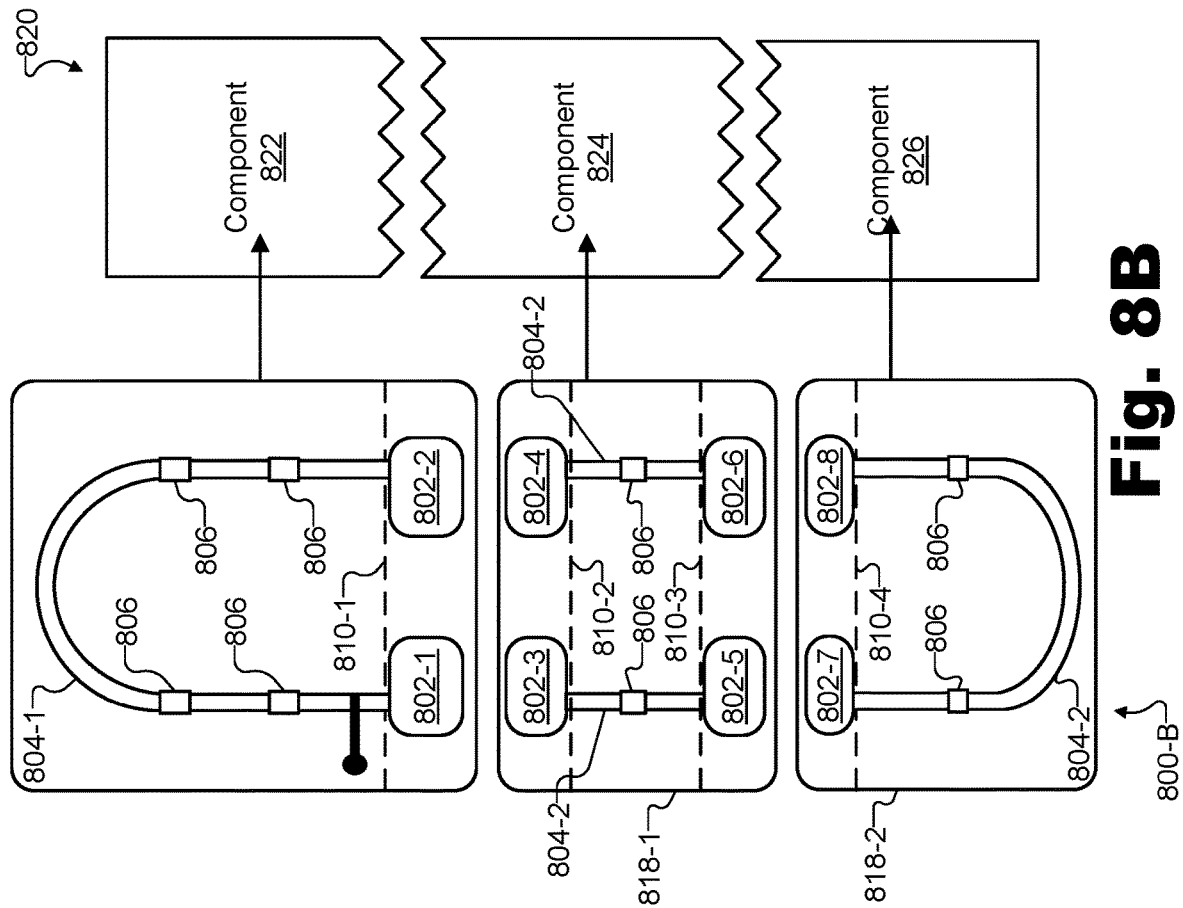
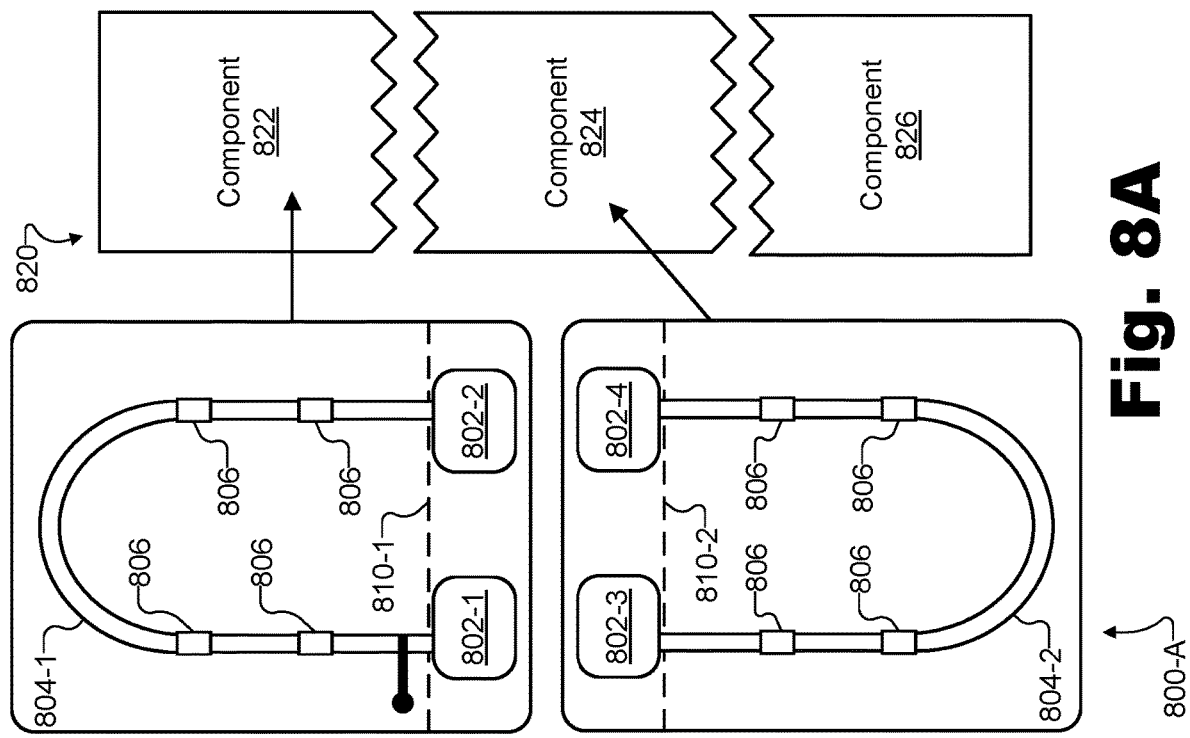
Fig. 8B
Fig. 8A

EXTENDED LENGTH ANTENNA ASSEMBLY FOR USE WITHIN A MULTI-COMPONENT SYSTEM

RELATED APPLICATIONS

The present application claims priority under 35 U.S.C. § 119(e) to U.S. Provisional Patent Application No. 62/556,265, filed on Sep. 8, 2017, and entitled "Extended Length Antenna Assembly for Use Within a Multi-Component System," the contents of which are hereby incorporated by reference in their entirety.

BACKGROUND INFORMATION

Information-carrying signals may be wirelessly transferred (i.e., transmitted and/or received) by way of various types of antennas such as loop antennas (e.g., folded dipole antennas, circular loop antennas, rectangular loop antennas, etc.), dipole antennas, monopole antennas, and so forth. In many applications, it may be desirable to transmit wireless signals using an antenna with the highest radiation efficiency possible. For instance, a highly efficient antenna may radiate a relatively large percentage of energy dedicated to driving the antenna to be wirelessly received by other antennas while storing or losing a relatively small percentage of the energy in the capacitance and/or inductance of the antenna, in reflections, in waste heat, and so forth.

One significant factor in how efficiently a loop antenna transmits a signal may be the antenna's size (e.g., diameter, circumference, etc.). For example, the radiation efficiency of certain loop antennas such as folded dipole antennas (e.g., loop antennas that are stretched along one dimension and compressed along another dimension to form a dipole antenna with an added conductor connecting the two ends to make a complete loop) may be significantly dependent on the length of the antenna. To achieve a high level of radiation efficiency, it may be desirable for a folded dipole antenna to have a length of approximately half of the wavelength of the signal that is being transferred by the antenna. Unfortunately, in certain systems, it may be difficult to fit antennas long enough to achieve high levels of radiation efficiency into relatively small enclosures housing the systems. As one specific example, various types of hearing systems (e.g., cochlear implant systems, hearing aid systems, earphone systems, etc.) may transmit wireless signals at frequencies having wavelengths significantly longer than the enclosures of the systems (e.g., frequencies in the 2.4 GHz spectrum used for BLUETOOTH technology or the like). As such, it may be difficult to design efficient antennas for use with such systems.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 8A and 8B illustrate exemplary configurations of how portions of an exemplary extended length loop antenna may be housed within different components of an exemplary multi-component system according to principles described herein.

DETAILED DESCRIPTION

Figure 1:
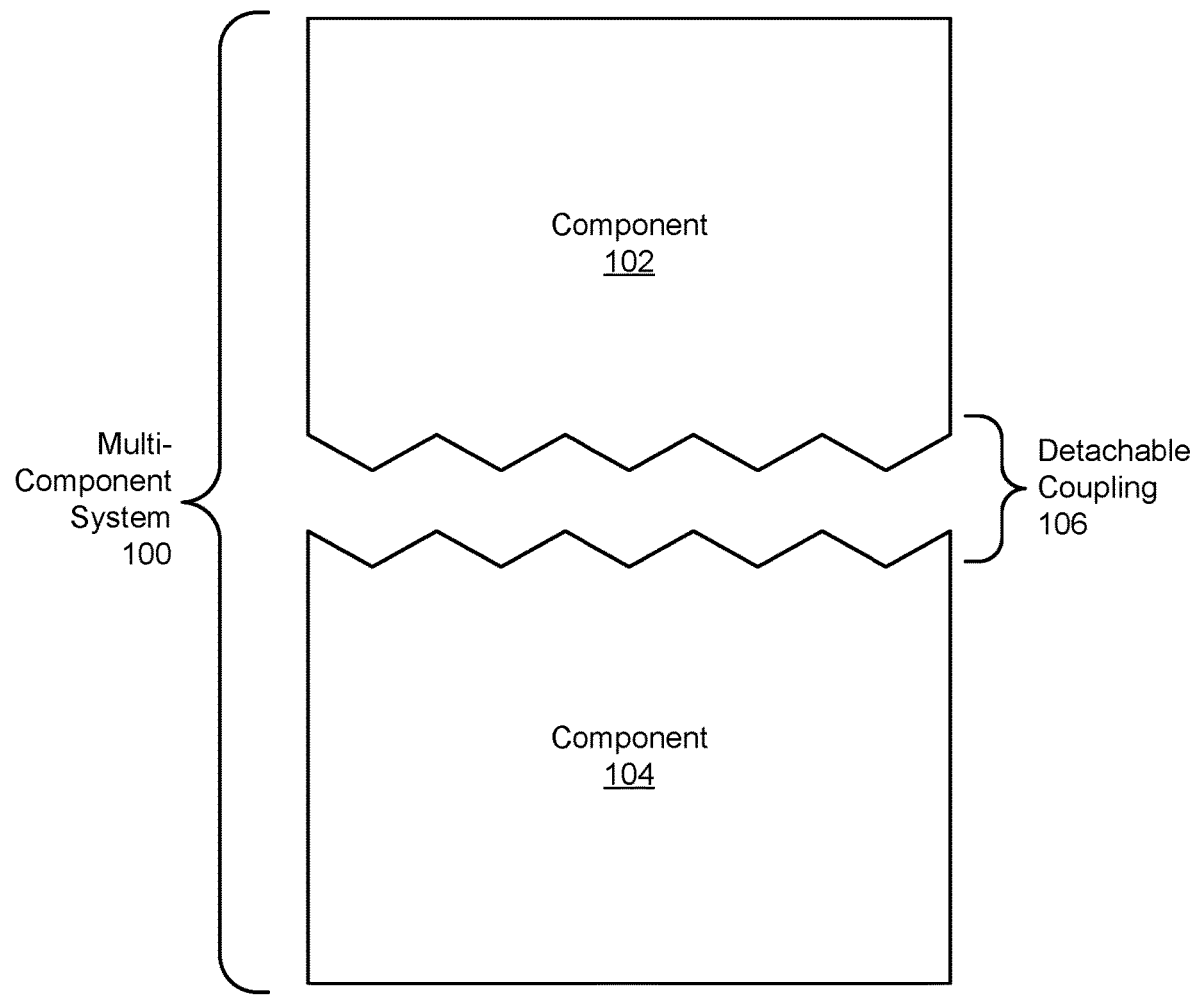
FIG. 1 illustrates an exemplary multi-component system according to principles described herein.

Extended length antenna assemblies for use within multi-component systems are described herein. As described above, it may be difficult to fit antennas long enough to achieve high levels of radiation efficiency into relatively small enclosures housing certain systems. For instance, as mentioned above, it may be desirable for various types of hearing systems (e.g., cochlear implant systems, hearing aid systems, earphone systems, etc.) to transmit wireless signals at frequencies having wavelengths significantly longer than the enclosures of the systems themselves. Unfortunately, it may not be possible for any particular component within such a system to house an antenna having a sufficient length to transmit at target frequencies with a relatively high efficiency. However, as will be disclosed in more detail herein, it may be possible to distribute different portions of an antenna assembly to be housed in two or more components of the system if the system is a multi-component system (i.e., a system including a plurality of distinct parts that may be detachably coupled with one another).

For example, as will be described in more detail below, an antenna assembly may include a first conductive pad and a second conductive pad housed within a first component of a multi-component system, as well as a first portion of a loop antenna housed within the first component and terminating on one side at the first conductive pad and on another side at the second conductive pad. The antenna assembly may further include a third conductive pad and a fourth conductive pad housed within a second component of the multi-component system (e.g., a component distinct from the first component and configured to detachably couple with the first component), as well as a second portion of the loop antenna housed within the second component and terminating on one side at the third conductive pad and on another side at the fourth conductive pad.

This extended length antenna assembly may be operable when the first and second components of the multi-component system are coupled (i.e., physically coupled) together. For example, when the first component is coupled with the second component, the first and third conductive pads may form a first non-galvanic coupling that capacitively couples the first and second portions of the loop antenna. Similarly, when the first and second components are coupled together, the second and fourth conductive pads may form a second non-galvanic coupling that further capacitively couples the first and second portions of the loop antenna. As used herein, a "non-galvanic coupling" may refer to a connection between two electrical elements (e.g., between conductive pads, etc.) that does not involve a direct, conductive connection over which current may flow. For instance, the non-galvanic couplings described above between the first and third conductive pads and between the second and fourth conductive pads may implement a capacitive (i.e., rather than a galvanic) coupling and, as such, may alternatively be referred to herein as "coupling capacitors." As a result, when the portions of the loop antenna are capacitively coupled together using these non-galvanic couplings, the first and second portions of the loop antenna remain galvanically separated such that there is not a conductive path (e.g., a path where direct current may flow) between the first and second portions of the loop antenna when the first component is coupled with the second component.

The extended length antenna assembly described above may be implemented in any suitable multi-component system having components, antenna portions, etc., of any size, shape, function, or the like as may serve a particular implementation. For example, as will be described in more detail below, an exemplary multi-component system may include a first component housing a first conductive pad, a second conductive pad, and a first portion of a loop antenna that terminates on one side at the first conductive pad and on another side at the second conductive pad. Moreover, the multi-component system may include a second component (e.g., a component distinct from the first component and configured to detachably couple with the first component) that houses a third conductive pad, a fourth conductive pad, and a second portion of the loop antenna that terminates on one side at the third conductive pad and on another side at the fourth conductive pad. In like manner to the antenna described above, when the first component is coupled with the second component in this exemplary multi-component system, the first and third conductive pads may form a first non-galvanic coupling that capacitively couples the first and second portions of the loop antenna, and the second and fourth conductive pads may form a second non-galvanic coupling that capacitively couples the first and second portions of the loop antenna.

Hearing systems such as cochlear implant systems, hearing aid systems, earphone systems, and/or other similar types of systems configured to provide or enhance hearing capabilities for users of the hearings systems are examples of multi-component systems that may benefit from the principles described herein. For example, an exemplary multi-component hearing system may include a sound processor component configured to process an audio signal and direct stimulation representative of the audio signal to be presented to a user of the multi-component hearing system, as well as a battery component distinct from the sound processor component and configured to detachably couple with the sound processor component to provide electrical power to the sound processor component. The sound processor component may house a first conductive pad, a second conductive pad, and a first portion of a loop antenna that terminates on one side at the first conductive pad and on another side at the second conductive pad, while the battery component may house a third conductive pad, a fourth conductive pad, and a second portion of the loop antenna that terminates on one side at the third conductive pad and on another side at the fourth conductive pad. As such, when the sound processor component is coupled with the battery component, the first and third conductive pads may form a first non-galvanic coupling that capacitively couples the first and second portions of the loop antenna, the second and fourth conductive pads may form a second non-galvanic coupling that capacitively couples the first and second portions of the loop antenna, and the first and second portions of the loop antenna may thus remain galvanically separated.

The extended length antenna assemblies for use within multi-component systems described herein may provide various benefits. For example, an extended length antenna assembly may significantly increase the radiation efficiency of a multi-component system (e.g., a hearing system such as a cochlear implant system, hearing aid system, earphone system, or the like) while allowing the system to remain relatively small (e.g., so as to conveniently be worn within or behind the ear of a user) and while avoiding bulky or cumbersome external antennas or the like. By increasing the radiation efficiency, multi-component systems may transmit signals more reliably by radiating a larger portion of energy. As such, the multi-component systems may benefit from an increased transmission range, an improved signal strength and reliability, a decrease in interference between systems (e.g., from the head in the case of a transmission between hearing systems communicating from locations associated with both ears of a user), an improved battery life, a decrease in heat being generated by the systems, a capability for smaller enclosures to house the systems, and so forth. Additionally, similar benefits may also arise when the extended length antenna assembly is used to receive wireless signals rather than to transmit them.

Additionally, the coupling together of different portions of the antenna assembly using capacitive coupling, rather than galvanic coupling, may be beneficial as well. For example, galvanic connections between components of a multi-component system may wear out with use, may corrode in the presence of moisture, and so forth. As such, by avoiding galvanic connections between components of a multi-component system, connectors between the components may be simplified and made more reliable. Similarly, the design of the antenna itself may be simplified and/or improved by using capacitive coupling rather than galvanic coupling.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary multi-component system 100. As shown multi-component system 100 includes a first component 102, a second component 104, and a detachable coupling 106 between components 102 and 104. Each of components 102 and 104 may be discrete components that may be configured to operate independently from one another and/or in conjunction with one another. For example, component 102 may be a primary component of multi-component system 100 and component 104 may be a battery component used to power the primary component. For instance, in one implementation, component 102 may represent a two-way radio device and component 104 may represent a detachable battery pack configured to connect to the two-way radio device to provide power for transmitting and receiving radio signals.

In other examples, component 102 may be a primary component and component 104 may be an accessory component that supports or enhances component 102 in some way (e.g., by adding additional functionality or the like). For example, in one implementation, component 102 may represent a computing device (e.g., a base of a laptop device, a tablet device, etc.) and component 104 may represent a device that augments the functionality of the computing device (e.g., the screen of the laptop device, a removable keyboard for the tablet device, etc.). In still other examples, components 102 and 104 may be associated with a sound processor assembly associated with a multi-component hearing system. Some of these examples will be described in more detail below.

As shown in FIG. 1, components 102 and 104 within multi-component system 100 may be coupled with one another by way of detachable coupling 106. When coupled, components 102 and 104 may interoperate with one another in any suitable way as may serve a particular implementation. For instance, in relation to the examples described above, component 104 may provide power or augmented functionality (e.g., a display screen, an external keyboard functionality, etc.) to component 102. When decoupled from one another, however, neither component 102 nor component 104 may be able to perform the same functionality that they can provide together.

In certain examples, detachable coupling 106 may be relatively permanent. For example, a laptop display screen may be relatively permanently coupled with a base of the laptop such that a user typically would not have cause to remove the screen unless, for instance, the screen was cracked and in need of repair or the like. Even still, because the laptop display screen may be detachable from the base of the laptop (e.g., by uncoupling the hinge using a specialized tool), the laptop may be considered to be a multi-component system, as the term is used herein, with a base component and a screen component that are detachably coupled.

In other examples, detachable coupling 106 may be configured to be much more temporary. For example, a battery pack component that connects to a primary device such as a sound processor of a hearing system or a radio may be configured to easily be removed so as to be changed out for a different battery pack, to be placed in a charger, to be reconfigured with fresh batteries, and so forth. Here again, because the battery pack component may be released from the primary component, the sound processor assembly or radio device may be considered to be a multi-component system as that term is used herein.

It will be recognized that although only two components (i.e., components 102 and 104) are illustrated in FIG. 1, multi-component system 100 may include any plurality of two or more components that each may be coupled (e.g., detachably coupled) with one another to form multi-component system 100. A few exemplary implementations of a multi-component system like multi-component system 100 will now be described. Specifically, a sound processor assembly within a cochlear implant system will be described in relation to FIGS. 2 and 3, a sound processor assembly within a hearing aid system will be described in relation to FIG. 4, and a sound processor assembly within an earphone system will be described in relation to FIG. 5.

Figure 2:
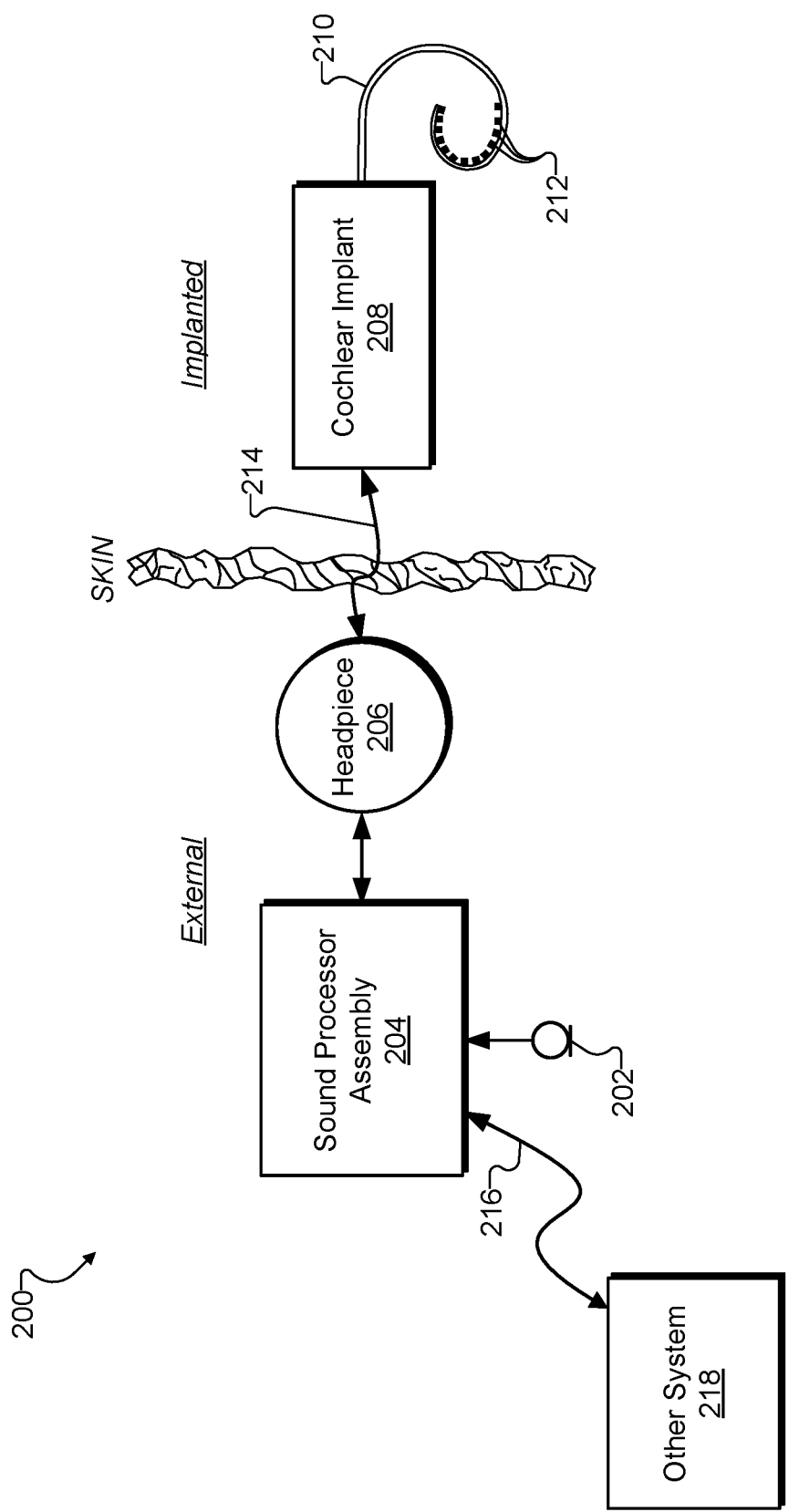
FIG. 2 illustrates an exemplary cochlear implant system according to principles described herein.

FIG. 2 illustrates an exemplary cochlear implant system 200. As shown, cochlear implant system 200 may include a microphone 202, a sound processor assembly 204, a headpiece 206 having a coil disposed therein, a cochlear implant 208, and an electrode lead 210. Electrode lead 210 may include an array of electrodes 212 disposed on a distal portion of electrode lead 210 and that are configured to be inserted into the cochlea to stimulate the cochlea after the distal portion of electrode lead 210 is inserted into the cochlea. It will be understood that one or more other electrodes (e.g., including a ground electrode, not explicitly shown) may also be disposed on other parts of electrode lead 210 (e.g., on a proximal portion of electrode lead 210) to, for example, provide a current return path for stimulation current generated by electrodes 212 and to remain external to the cochlea after electrode lead 210 is inserted into the cochlea. As shown, electrode lead 210 may be pre-curved so as to properly fit within the spiral shape of the cochlea. Additional or alternative components may be included within cochlear implant system 200 as may serve a particular implementation.

As shown, cochlear implant system 200 may include various components configured to be located external to a patient including, but not limited to, microphone 202, sound processor assembly 204, and headpiece 206. Cochlear implant system 200 may further include various components configured to be implanted within the patient including, but not limited to, cochlear implant 208 and electrode lead 210.

Microphone 202 may be configured to detect audio signals presented to the user. Microphone 202 may be implemented in any suitable manner. For example, microphone 202 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor assembly 204. Additionally or alternatively, microphone 202 may be implemented by one or more microphones disposed within headpiece 206, one or more microphones disposed within sound processor assembly 204, one or more beam-forming microphones, and/or any other suitable microphone as may serve a particular implementation.

Sound processor assembly 204 may include a sound processor component and a battery component, as well as, in certain implementations, one or more other components such as an earhook component associated with sound processor assembly 204, a cable component associated with sound processor assembly 204 (e.g., a cable communicatively coupling sound processor assembly 204 with headpiece 206), an extension unit component, or another suitable accessory. The sound processor component included within sound processor assembly 204 may be configured to process an audio signal (e.g., an acoustic audio signal detected by microphone 202, an electrical audio signal input by way of an auxiliary audio input port or a Clinician's Programming Interface ("CPI") device, etc.) and to direct stimulation representative of the audio signal to be presented to a user of cochlear implant system 200. For example, the stimulation representative of the audio signal and directed by the sound processor component to be presented to the user may be electrical stimulation presented by way of cochlear implant 208 implanted within the user, as will be described below.

The battery component of sound processor assembly 204 may be distinct from the sound processor component and configured to detachably couple with the sound processor component to provide electrical power to the sound processor component. As such, sound processor assembly 204, alone or together with the rest of cochlear implant system 200, may implement multi-component system 100 with, for instance, the sound processor component acting as component 102, the battery component acting as component 104, and a connection between the sound processor component and the battery component acting as detachable coupling 106.

When sound processor assembly 204 is properly assembled such that the sound processor component, the battery component, and any other components included in the assembly are coupled together, sound processor assembly 204 may be configured to direct cochlear implant 208 to generate and apply electrical stimulation (also referred to herein as "stimulation current") representative of an audio signal to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor assembly 204 may process the audio signal in accordance with a selected sound processing strategy or program to generate appropriate stimulation parameters for controlling cochlear implant 208. The components of sound processor assembly 204 may each be housed within any suitable housing (e.g., configured to couple together to form a behind-the-ear ("BTE") unit, a body worn unit, or the like).

In some examples, sound processor assembly 204 may wirelessly transmit stimulation parameters (e.g., in the form of data words included in a forward telemetry sequence) and/or power to cochlear implant 208 by way of a wireless communication link 214 between headpiece 206 and cochlear implant 208 (e.g., a wireless link between a coil disposed within headpiece 206 and a coil included within or coupled to cochlear implant 208). To this end, headpiece 206 may be communicatively coupled to sound processor assembly 204 and may include an antenna (e.g., a coil and/or one or more wireless communication components) configured to facilitate selective wireless coupling of sound processor assembly 204 to cochlear implant 208. Additionally or alternatively, headpiece 206 may be used to selectively and wirelessly couple any other external device (e.g., a battery charger, etc.) to cochlear implant 208. Headpiece 206 may be configured to be affixed to the patient's head and positioned or aligned such that an antenna housed within headpiece 206 is communicatively coupled to a corresponding implantable antenna (which may also be implemented by a coil and/or one or more wireless communication components) included within or otherwise associated with cochlear implant 208. In this manner, stimulation parameters and/or power signals may be wirelessly transferred between sound processor assembly 204 and cochlear implant 208 via wireless communication link 214.

It will be understood that wireless communication link 214 may be distinct and separate from one or more other wireless communications links (e.g., communication links over a BLUETOOTH interface, a Wi-Fi interface or other such communication interface) that sound processor assembly 204 may have with other devices. For example, as shown, sound processor assembly 204 may have an additional wireless communication link 216 (e.g., a BLUETOOTH link, a Wi-Fi link, etc.) with another system 218 (e.g., with another sound processor assembly in a binaural cochlear implant system, with a computing device or mobile device providing an audio signal to sound processor assembly 204, etc.). Communication over wireless communication link 216 may take place by way of an extended length antenna assembly (i.e., rather than by way of a coil within headpiece 206), and will be described in more detail below. It will be understood that communication links 214 and 216 may both include a bi-directional communication link and/or one or more dedicated uni-directional communication links.

Cochlear implant 208 may include any type of implantable stimulator that may be used in association with the systems and methods described herein. For example, cochlear implant 208 may be implemented by an implantable cochlear stimulator. In some alternative implementations, cochlear implant 208 may include a brainstem implant and/or any other type of cochlear implant that may be implanted within a patient and configured to apply stimulation to one or more stimulation sites located along an auditory pathway of a patient.

In some examples, cochlear implant 208 may be configured to generate electrical stimulation representative of an audio signal processed by sound processor assembly 204 (e.g., an audio signal detected by microphone 202) in accordance with one or more stimulation parameters transmitted thereto by sound processor assembly 204. Cochlear implant 208 may be further configured to apply the electrical stimulation to one or more stimulation sites (e.g., one or more intracochlear regions) within the patient via electrodes 212 disposed along electrode lead 210. In some examples, cochlear implant 208 may include a plurality of independent current sources each associated with a channel defined by one or more of electrodes 212. In this manner, different stimulation current levels may be applied to multiple stimulation sites simultaneously by way of multiple electrodes 212.

Figure 3:
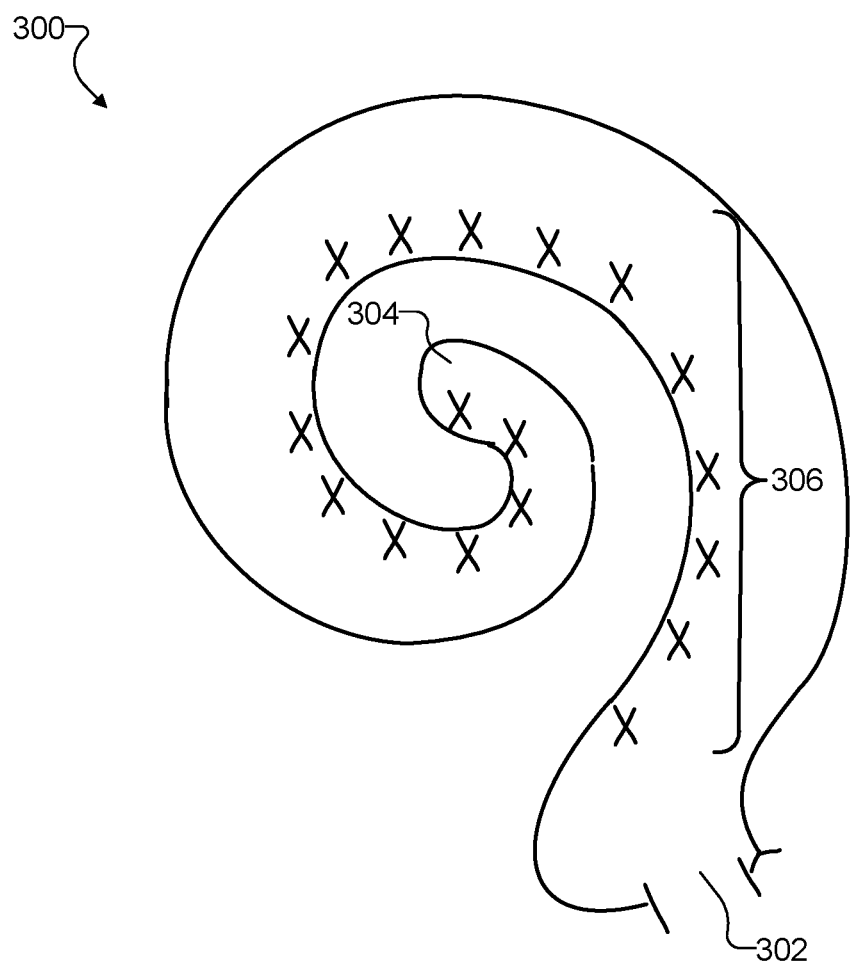
FIG. 3 illustrates a schematic structure of the human cochlea according to principles described herein.

FIG. 3 illustrates a schematic structure of the human cochlea 300 into which electrode lead 210 may be inserted. As shown in FIG. 3, cochlea 300 is in the shape of a spiral beginning at a base 302 and ending at an apex 304. Within cochlea 300 resides auditory nerve tissue 306, which is denoted by Xs in FIG. 3. The auditory nerve tissue 306 is organized within the cochlea 300 in a tonotopic manner. Relatively low frequencies are encoded at or near the apex 304 of the cochlea 300 (referred to as an "apical region") while relatively high frequencies are encoded at or near the base 302 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the electrode lead, the anatomy of the patient's cochlea, and/or any other factor as may serve a particular implementation.

Figure 4:
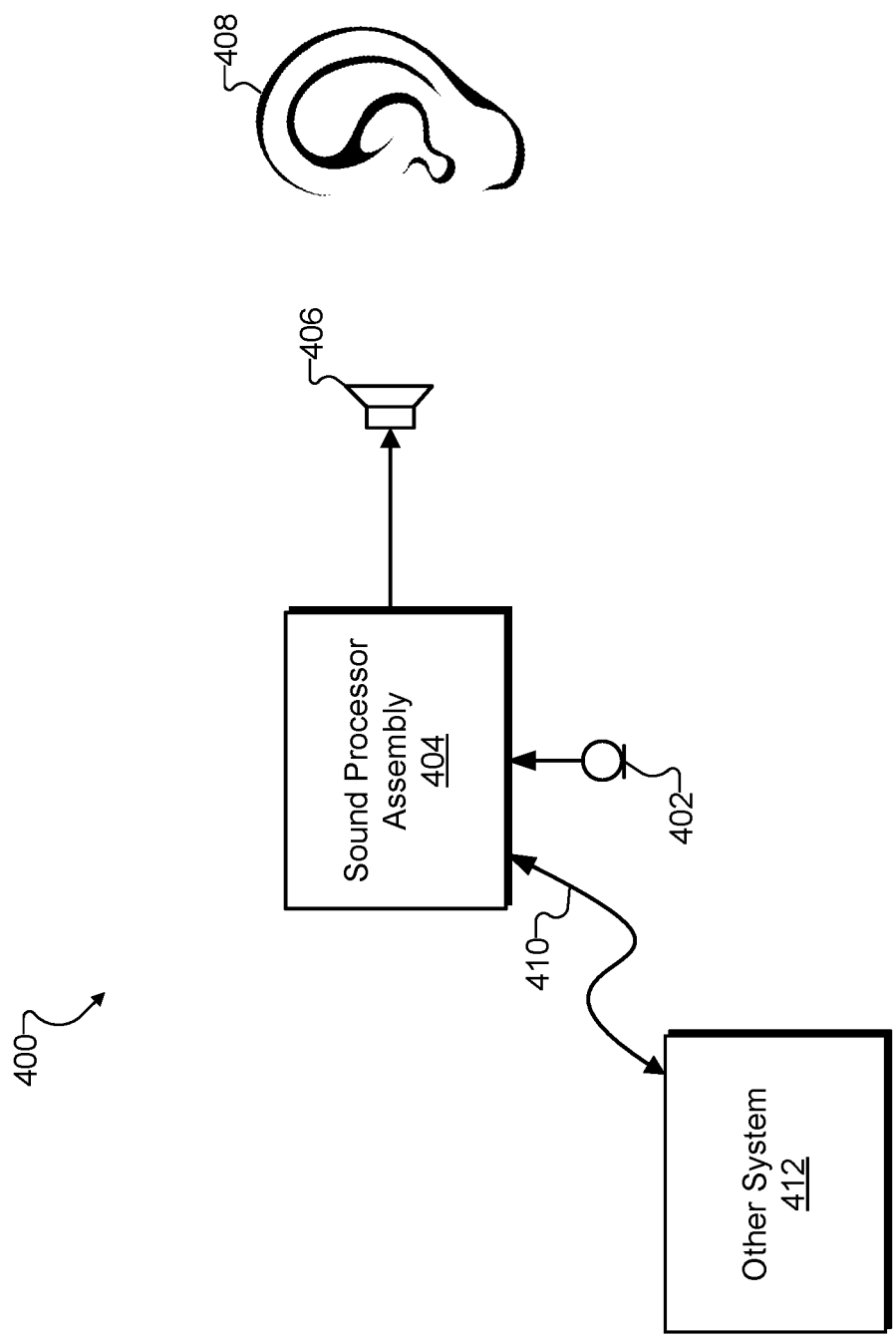
FIG. 4 illustrates an exemplary hearing aid system according to principles described herein.

To illustrate another exemplary multi-component hearing system, FIG. 4 shows an exemplary hearing aid system 400. As shown, hearing aid system 400 may include a microphone 402, a sound processor assembly 404, and a loudspeaker 406. Additional or alternative components may be included within hearing aid system 400 as may serve a particular implementation.

As with microphone 202 described above in relation to cochlear implant system 200, microphone 402 may be configured to detect audio signals presented to the user and may be implemented in any of the ways described above.

Similarly, as with sound processor assembly 204 described above, sound processor assembly 404 may include a sound processor component and a battery component, as well as, in certain implementations, other components such as an extension unit component or other accessory. Like sound processor assembly 204, the sound processor component included within sound processor assembly 404 may be configured to process an audio signal (e.g., an acoustic audio signal detected by microphone 402, an electrical audio signal input by way of an auxiliary audio input port, etc.) and to direct stimulation representative of the audio signal to be presented to a user of hearing system 400. For example, the stimulation representative of the audio signal and directed by the sound processor component to be presented to the user may be acoustic stimulation presented by way of loudspeaker 406 associated with (e.g., placed within or near to) an ear 408 of the user.

As described with the battery component of sound processor assembly 204, the battery component of sound processor assembly 404 may be distinct from the sound processor component and configured to detachably couple with the sound processor component to provide electrical power to the sound processor component. As such, sound processor assembly 404, alone or together with the rest of hearing aid system 400, may implement multi-component system 100 with, for instance, the sound processor component acting as component 102, the battery component acting as component 104, and a connection between the sound processor component and the battery component acting as detachable coupling 106.

When sound processor assembly 404 is properly assembled such that the sound processor component, the battery component, and any other components included in the assembly are coupled together, sound processor assembly 404 may be configured to direct loudspeaker 406 to generate acoustic stimulation representative of an audio signal to be presented to the user at ear 408.

Similar to wireless communication link 216 to other system 218 described above, FIG. 4 illustrates that hearing aid system 400 (e.g., and, in particular, sound processor assembly 404) may have one or more wireless communication links (e.g., communication links over a BLUETOOTH interface, Wi-Fi interface, or other such communication interface) with other devices. Specifically, for example, FIG. 4 shows that sound processor assembly 404 may have a wireless communication link 410 (e.g., a BLUETOOTH link, a Wi-Fi link, etc.) with another system 412 (e.g., with another sound processor assembly in a binaural hearing aid system or hybrid cochlear implant/hearing aid system, with a computing device or mobile device providing an audio signal to sound processor assembly 404, etc.). Communication over wireless communication link 410 may take place by way of an extended length antenna assembly, as will be described in more detail below. It will be understood that communication link 410 may include a bi-directional communication link and/or one or more dedicated uni-directional communication links.

Figure 5:
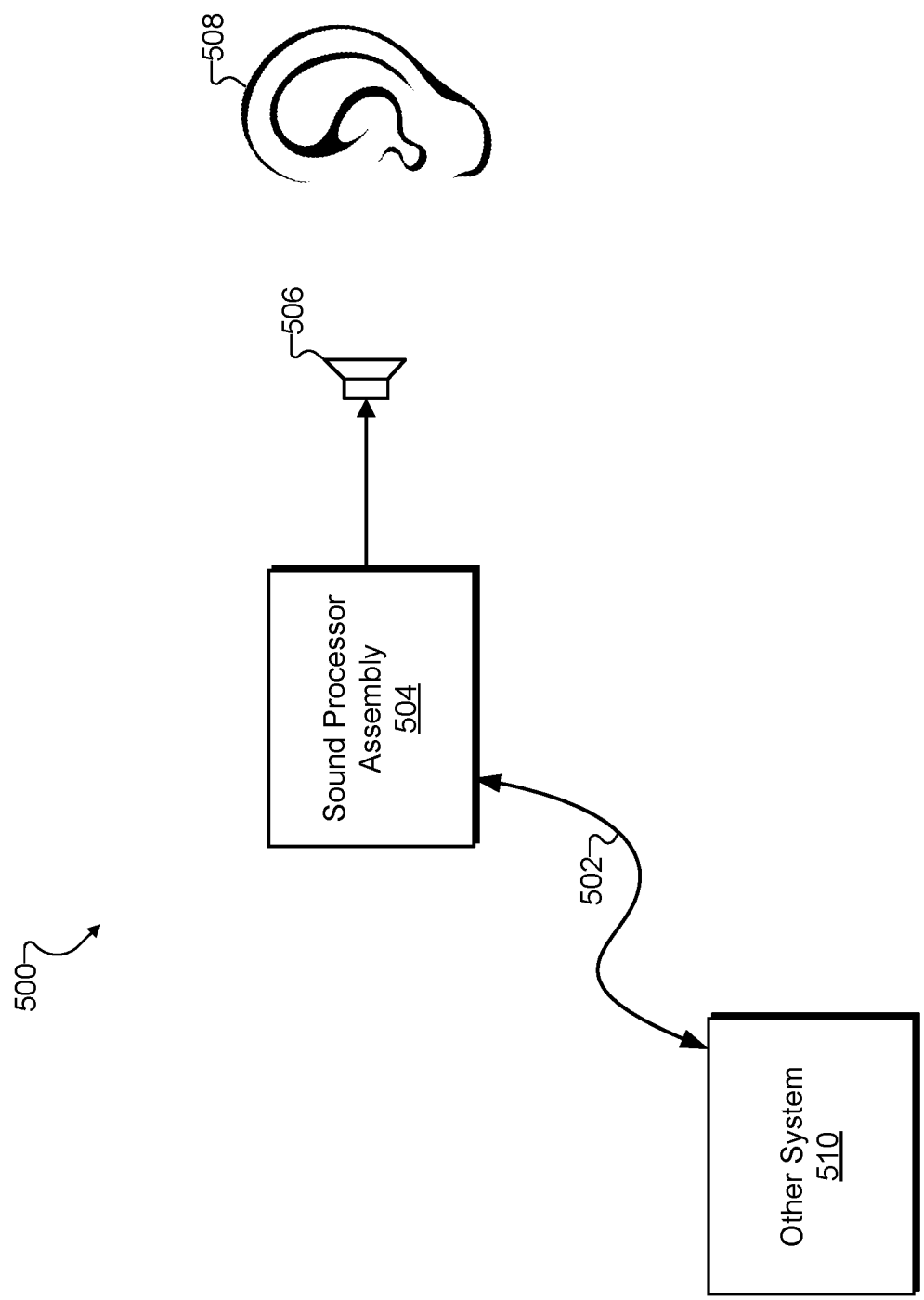
FIG. 5 illustrates an exemplary earphone system according to principles described herein.

To illustrate another exemplary multi-component hearing system, FIG. 5 shows an exemplary earphone system 500. As shown, earphone system 500 may receive audio input from a wireless communication link 502 into a sound processor assembly 504, which may be used to generate and present an acoustic audio signal by way of a loudspeaker 506 to an ear 508 of a user of earphone system 500. Additional or alternative components may be included within earphone system 500 as may serve a particular implementation.

While cochlear implant system 200 and hearing aid system 400 described above received audio input from microphones (i.e., from microphones 202 and 402, respectively) and/or other sources, earphone system 500 may be configured to receive audio input exclusively by way of wireless communication link 502 with another system 510 (e.g., with another sound processor assembly in a binaural earphone system, with a computing device or mobile device providing an audio signal to sound processor assembly 504, etc.). For example, as opposed to detecting ambient sounds presented to the user by way of a microphone to enable or facilitate the user's hearing as systems 200 and 400 may be configured to do, earphone system 500 may receive audio unrelated to ambient sounds around the user such as music or other entertainment provided by an audio or video player implemented by other system 510.

As with sound processor assemblies 204 and 404 described above, sound processor assembly 504 may include a sound processor component and a battery component, as well as, in certain implementations, other components such as an extension unit component or other accessory. Like sound processor assemblies 204 and 404, the sound processor component included within sound processor assembly 504 may also be configured to process an audio signal (e.g., a wireless electrical audio signal received by the sound processor component such as from an audio player, a wired electrical audio signal input by way of an auxiliary audio input port, etc.) and to direct stimulation representative of the audio signal to be presented to a user of earphone system 500. For example, the stimulation representative of the audio signal and directed by the sound processor component to be presented to the user may be acoustic stimulation presented by way of loudspeaker 506 associated with (e.g., placed within or near to) ear 508 of the user.

As described with the battery components of sound processor assemblies 204 and 404, the battery component of sound processor assembly 504 may be distinct from the sound processor component and configured to detachably couple with the sound processor component to provide electrical power to the sound processor component. As such, sound processor assembly 504, alone or together with the rest of earphone system 500, may implement multi-component system 100 with, for instance, the sound processor component acting as component 102, the battery component acting as component 104, and a connection between the sound processor component and the battery component acting as detachable coupling 106.

When sound processor assembly 504 is properly assembled such that the sound processor component, the battery component, and any other components included in the assembly are coupled together, sound processor assembly 504 may be configured to direct loudspeaker 506 to generate acoustic stimulation representative of an audio signal to be presented to the user at ear 508. Wireless communication link 502 may represent any suitable link (e.g., a BLUETOOTH link, a Wi-Fi link, etc.) that may be used to wirelessly communicate audio data with other system 510 in a particular implementation. Communication over wireless communication link 502 may take place by way of an extended length antenna assembly, as will be described in more detail below. It will be understood that communication link 502 may include a bi-directional communication link and/or one or more dedicated uni-directional communication links.

As described above, various types of multi-component hearing systems (e.g., systems 200, 400, 500, etc.) and/or other types of multi-component systems may transmit and receive signals using wireless communication technologies such as BLUETOOTH, Wi-Fi, and the like. In the case of a BLUETOOTH connection, for example, this means that these multi-component systems may transmit and receive wireless signals on a 2.4 GHz spectrum of frequencies from approximately 2.400 GHz to approximately 2.485 GHz. Accordingly, the wavelength of such signals (i.e., calculated as the speed of light divided by the frequency) may be approximately 121-125 millimeters (mm). Certain antennas (e.g., dipole antennas, etc.) shorter than about one half of these wavelengths (i.e., shorter than about 61-63 mm) may be considered to be "electrically short" antennas for such frequencies and, as such, may transmit signals with a relatively low radiation efficiency and/or be associated with other drawbacks and challenges. Thus, it may be desirable for frequencies in the 2.4 GHz spectrum used for BLUETOOTH communications to be generated by an antenna that is a target length of approximately 61-63 mm or longer.

Unfortunately, many current hearing systems do not include any single component (e.g., including a sound processor component) that is at least the target length for BLUETOOTH, as described above (i.e., 61-63 mm or longer). In many cases, this is because users desire that components of the hearing systems be designed to be as small and discreet as possible (e.g., so as to fit within the ear, to be worn comfortably and inconspicuously behind the ear, etc.). For example, BTE sound processors for certain cochlear implant systems and/or other hearing systems may be long enough to house an antenna only about 30-40 mm long, which is significantly shorter than the target length for the 2.4 GHz BLUETOOTH spectrum. However, while such sound processor components alone may be too short to house an antenna with a target length (e.g., for the BLUETOOTH wavelength or another particular wavelength), entire sound processor assemblies (i.e., each including a sound processor component, a battery component, and possibly one or more other components), when assembled, may be significantly longer (i.e., at least as long as the target length for BLUETOOTH).

Consequently, as mentioned above, multi-component systems such as the multi-component hearing systems (e.g., sound processor assemblies) described above and/or other multi-component systems may house communicatively coupled portions of extended length loop antenna assemblies as described herein. In this way, the multi-component system may benefit from having high radiation efficiencies even if each individual component of the multi-component system is significantly shorter than a target length for a particular frequency at which data is to be transferred such that no individual component alone may be capable of housing an antenna associated with a relatively high radiation efficiency.

Figure 6:
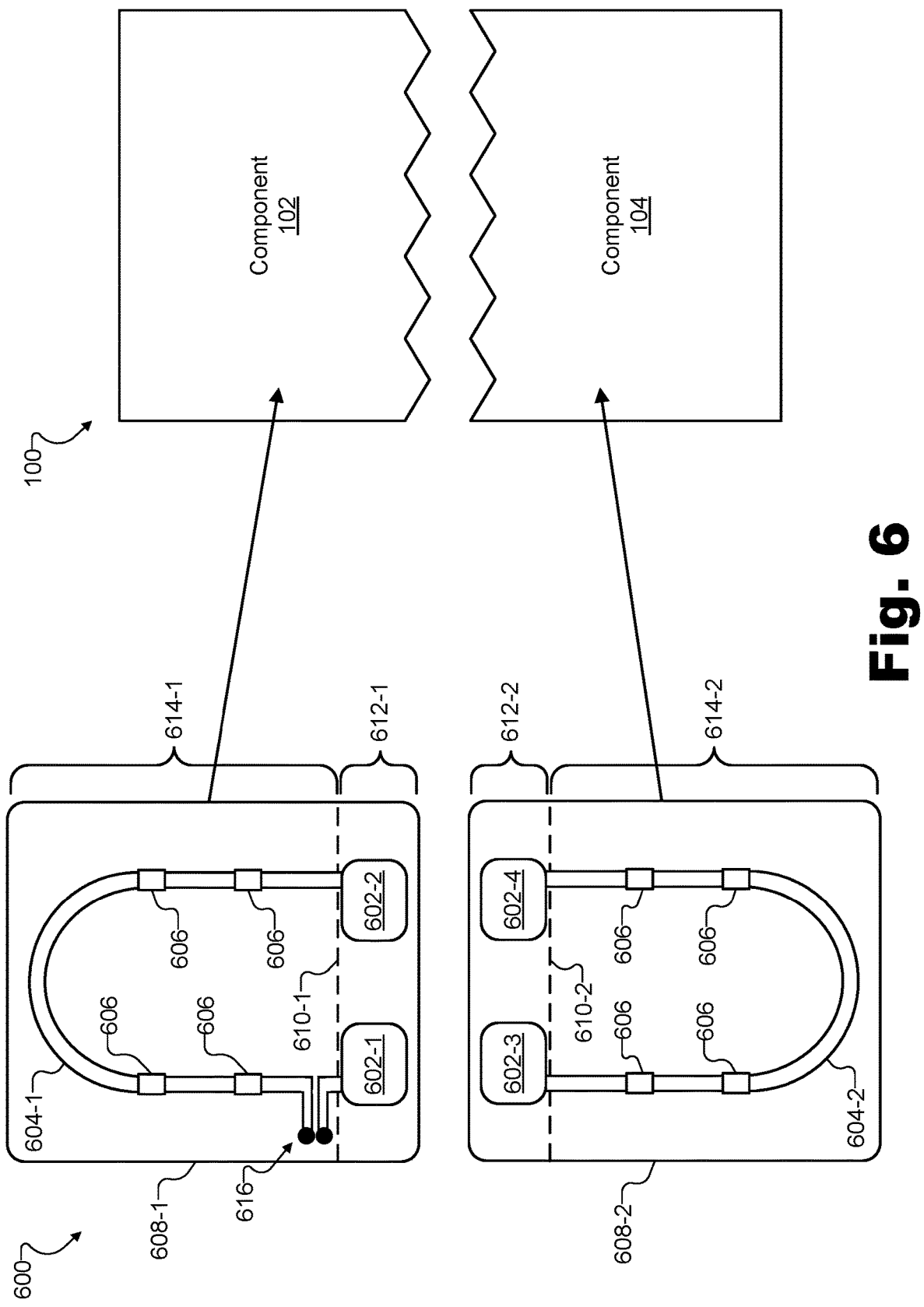
FIG. 6 illustrates an exemplary extended length loop antenna having a plurality of portions each configured to be housed in a different component of the multi-component system of FIG. 1 according to principles described herein.

To illustrate, FIG. 6 shows an exemplary extended length loop antenna having a plurality of portions each configured to be housed in a different component of multi-component system 100 (e.g., implemented as a sound processor assembly in one of systems 200, 400, or 500, or as another suitable multi-component system). Specifically, as shown in FIG. 6, an antenna assembly 600 includes two conductive pads 602 (i.e., a first conductive pad 602-1 and a second conductive pad 602-2), as well as a first portion 604-1 of a loop antenna terminating on one side at first conductive pad 602-1 and terminating on the other side at second conductive pad 602-2. As shown, conductive pads 602-1 and 602-2 and portion 604-1 of the loop antenna are configured to be housed within component 102 of multi-component system 100.

Antenna assembly 600 further includes two additional conductive pads 602 (i.e., a third conductive pad 602-3 and a fourth conductive pad 602-4) and a second portion 604-2 of the loop antenna that terminates on one side at third conductive pad 602-3 and on the other side at fourth conductive pad 602-4. As shown, conductive pads 602-3 and 602-4 and portion 604-2 of the loop antenna are configured to be housed within component 104 of multi-component system 100, which, as described above, may be distinct from component 102 and configured to detachably couple with component 102.

For antenna assembly 600 to operate properly, both portions 604 of the loop antenna may be configured to be capacitively coupled when components 102 and 104 are coupled together. Specifically, for instance, when component 102 is coupled with component 104, conductive pads 602-1 and 602-3 may form a first non-galvanic coupling (i.e., a first coupling capacitor) that capacitively couples portions 604-1 and 604-2 of the loop antenna, while conductive pads 602-2 and 602-4 may form a second non-galvanic coupling (i.e., a second coupling capacitor) that capacitively couples portions 604-1 and 604-2 of the loop antenna. Although portions 604-1 and 604-2 may thus be capacitively and electrically coupled so as to allow antenna assembly 600 to operate as a loop antenna (e.g., a folded dipole antenna in the example illustrated in FIG. 6), it will be understood that portions 604-1 and 604-2 of the loop antenna may remain galvanically separated when components 102 and 104 are coupled. As such, while alternating currents may freely pass through the non-galvanic couplings during operation of the loop antenna, direct currents may not have any conductive path to flow from portion 604-1 to portion 604-2 of the loop antenna or vice versa.

It will be understood that the non-galvanic couplings (i.e., coupling capacitors) formed by conductive pads 602 may not include or refer to any discrete capacitor components (i.e., capacitor components designed, packaged, and used in a circuit as such). Rather, the capacitance of these coupling capacitors may be formed exclusively by conductive pads 602 (which, as will be described in more detail below, may be turned to face one another in parallel) and a natural dielectric between them (e.g., air, material from which the enclosures housing components 102 and 104 are constructed, etc.) when components 102 and 104 are coupled.

In certain examples, the coupling together of components 102 and 104 described above, where conductive pads 602-1 and 602-3 form the first non-galvanic coupling and conductive pads 602-2 and 602-4 form the second non-galvanic coupling, may be just one configuration (e.g., a standard configuration) of multiple possible configurations for the connection between components 102 and 104. For instance, in these examples, component 104 may be configured to reversibly and detachably couple with component 102 in at least one other configuration (e.g., a reverse configuration distinct from the standard configuration). When component 102 is coupled with component 104 in a reverse configuration, portion 604-2 of the loop antenna may be flipped such that conductive pads 602-1 and 602-4 form the first non-galvanic coupling that capacitively couples portions 604-1 and 604-2 of the loop antenna, and conductive pads 602-2 and 602-3 form the second non-galvanic coupling that capacitively couples portions 604-1 and 604-2 of the loop antenna. Again, in the reverse configuration as in the standard configuration, portions 604-1 and 604-2 of the loop antenna may remain galvanically separated when components 102 and 104 are coupled together.

Along with capacitively coupling portions 604-1 and 604-2 of the loop antenna without any galvanic connections between portions 604-1 and 604-2, the first and second non-galvanic couplings (i.e., the first and second coupling capacitors) formed by conductive pads 602 may also serve other functions. For example, the coupling capacitors formed by conductive pads 602 may be configured so as to be matched to the inductance of the loop antenna. In this way, the coupling capacitors may help the loop antenna to resonate efficiently (e.g., to radiate as much energy as possible and store as little as possible), to minimize losses, and so forth.

As further illustrated in FIG. 6, some of the functions performed by the coupling capacitor to resonate the antenna, eliminate reflections, and otherwise improve the functionality and efficiency of the antenna may be further performed by one or more discrete capacitors 606. Specifically, for instance, antenna assembly 600 may further include discrete capacitors 606 connected in series along at least one of portions 604-1 and 604-2 of the loop antenna. Discrete capacitors 606 may be collectively configured to resonate with an inductance of the loop antenna at a carrier frequency (e.g., a transmission frequency) at which data is transferred (e.g., transmitted, received, etc.) by way of the loop antenna. For example, discrete capacitors 606 may, in combination with the first and second coupling capacitors formed by conductive pads 602, be matched to the inductance the loop antenna to maximize the radiation efficiency and minimize the amount of energy stored within capacitance or inductance of the loop antenna.

While one or two capacitors (e.g., the coupling capacitors formed by conductive pads 602) may theoretically be configured to properly minimize reflections and allow the loop antenna to properly resonate, it may be advantageous, in certain examples as shown, to use a larger plurality of capacitors to perform these functions collectively. For example, while a manufacturing tolerance for a typical discrete capacitor may be 1% (i.e., meaning that the value marked on the package of the capacitor could be up to 1% higher or lower than the actual value of the capacitor), the combined tolerance for a plurality of such capacitors may be dramatically reduced. For example, the tolerance for the average capacitor in a group of ten 1% tolerance capacitors used collectively may be 0.1%. Accordingly, in some examples, several discrete capacitors 606 may be used and distributed in a balanced or symmetrical fashion around the loop antenna (e.g., such that both portions 604 of the loop antenna have equal numbers of discrete capacitors 606, such that both sides of each portion 604 of the loop antenna have equal numbers of discrete capacitors 606, etc.).

Moreover, conductive pads 602 may also be sized, spaced, and/or otherwise configured such that the non-galvanic couplings formed by conductive pads 602 act as coupling capacitors that are also matched with the values of discrete capacitors 606 (i.e., so that the coupling capacitors have a similar or identical electrical effect in the antenna circuit as any or all of discrete capacitors 606. In other words, for example, each of discrete capacitors 606 may be connected in series along one of portions 604-1 or 604-2 of the loop antenna have a capacitance matched to a capacitance of the first non-galvanic coupling (i.e., the first coupling capacitor formed by conductive pads 602-1 and 602-3) and to a capacitance of the second non-galvanic coupling (i.e., the second coupling capacitor formed by conductive pads 602-2 and 602-4).

Antenna assembly 600 may be implemented in any way as may serve a particular implementation. For instance, in some examples, antenna assembly 600 may be implemented using a first flexible printed circuit board ("PCB") 608-1 upon which portion 604-1 of the loop antenna and conductive pads 602-1 and 602-2 are implemented, and a second flexible PCB 608-2 upon which portion 604-2 of the loop antenna and conductive pads 602-3 and 604-4 are implemented. As shown, flexible PCB 608-1 may thus be housed within component 102 (e.g., within a sound processor component of a multi-component hearing system) and flexible PCB 608-2 may be housed within component 104 (e.g., within a battery component of the multi-component hearing system).

As shown, flexible PCB 608-1 may include a first fold 610-1 forming an angle between a part 612-1 of flexible PCB 608-1 upon which conductive pads 602-1 and 602-2 are implemented and a part 614-1 of flexible PCB 608-1 upon which portion 604-1 of the loop antenna is implemented. While fold 610-1 is illustrated as a dotted line in FIG. 6, it will thus be understood that part 612-1 of flexible PCB 608-1 may be at an angle (e.g., at an approximately perpendicular angle) to part 614-1 due to fold 610-1. This angle is more easily illustrated from a perspective view of antenna assembly 600 (as opposed to the straight-on view of FIG. 6) and will be illustrated and described in more detail below. Similar to flexible PCB 608-1, flexible PCB 608-2 may include a second fold 610-2 forming an angle between a part 612-2 of flexible PCB 608-2 upon which conductive pads 602-3 and 602-4 are implemented and a part 614-2 of flexible PCB 608-2 upon which portion 604-2 of the loop antenna is implemented. While flexible PCBs 608 are illustrated in FIG. 6, it will be understood that antenna assembly 600 may be implemented in any suitable way including by each of parts 612 and 614 being implemented on multiple separate PCBs connected by a conductor, by wire that bends at folds 610, or by any other materials or configurations as may serve a particular implementation.

It will also be understood that, while FIG. 6 only illustrates flexible PCBs containing features and components associated with antenna assembly 600, other PCBs and/or circuitry may also be included within components 102 and/or 104 as may serve a particular implementation. For example, a PCB upon which power, processing, and/or transmission circuitry and chips are implemented may be communicatively coupled with flexible PCBs 608 and/or other parts of antenna assembly 600 as may serve a particular implementation. As shown in FIG. 6, for instance, other circuitry may drive the loop antenna of antenna assembly 600 by way of a feed line 616 that allows access to antenna assembly 600 for a communication chip. As illustrated, feed line 616 may be associated with two distinct inputs (i.e., associated with two separate pins), allowing access to antenna assembly 600 by the communication chip at two distinct points along antenna assembly 600. Such distinct inputs may be used to properly drive the loop antenna of antenna assembly 600 while other types of antennas (e.g., monopole antennas) in other antenna assemblies may be properly driven by only a single input feed line (e.g., a feed line associated with a single pin).

As described above, when component 102 (e.g., implemented as a sound processor component of one of multi-component hearing systems 200, 400, or 500) is coupled with component 104 (e.g., implemented as a battery component or other component of one of the multi-component hearing systems), conductive pads 602-1 and 602-3 form a first non-galvanic coupling and conductive pads 602-2 and 602-4 form a second non-galvanic coupling to capacitively couple portions 604-1 and 604-2 of the loop antenna, all while portions 604-1 and 604-2 remain galvanically separated. To illustrate how these non-galvanic couplings are formed in an exemplary sound processor assembly of an exemplary multi-component hearing system (e.g., a system analogous to one of systems 200, 400, or 500, described above), FIG. 7 shows a perspective view of a multi-component hearing system 700 housing antenna assembly 600.

Multi-component hearing system 700 may be an implementation of any of systems 200, 400, and/or 500, or of a component or components included therein. For instance, multi-component hearing system 700 may represent an implementation of one of sound processor assemblies 204, 404, and/or 504. Accordingly, as shown, multi-component hearing system 700 may include a sound processor component 702 configured to physically and communicatively couple with a battery component 704 by way of a connection mechanism 706 that mechanically facilitates the coupling of components 702 and 704 and may provide one or more connections between components 702 and 704 when coupled. For example, connection pins built into or otherwise associated with connection mechanism 706 may provide galvanic connections by way of which power, data, or other signals may be transferred from battery component 704 to sound processor component 702 or from sound processor component 702 to battery component 704. Multi-component hearing system 700 may also include an earhook component 708 used to hold multi-component hearing system 700 in place behind an ear of a user in certain implementations.

Conductive pads 602 may be coupled together to form non-galvanic couplings when components 702 and 704 are coupled together by way of connection mechanism 706. Specifically, as shown, sound processor component 702 houses flexible PCB 608-1 upon which conductive pads 602-1 and 602-2 and portion 604-1 of a loop antenna are implemented. (It will be understood that one or more additional discrete capacitors 606 may also be included on flexible PCB 608-1 as shown in FIG. 6, although this detail is omitted from FIG. 7.) As described above in relation to FIG. 6, flexible PCB 608-1 includes part 612-1 upon which conductive pads 602-1 and 602-2 are implemented and part 614-1 upon which portion 604-1 of the loop antenna is implemented. Parts 612-1 and 614-1 are separated by a fold 610-1 in flexible PCB 608-1 that positions part 612-1 approximately perpendicular to part 614-1 so as to be parallel with and to face part 612-2 upon which the other conductive pads 602 are included. Similarly, as further shown, battery component 704 houses flexible PCB 608-2 upon which conductive pads 602-3 and 602-4 and portion 604-2 of the loop antenna are implemented. (Again, it will be understood that one or more additional discrete capacitors 606 may also be included on flexible PCB 608-2 as shown in FIG. 6.) As described above in relation to FIG. 6, flexible PCB 608-2 includes part 612-2 upon which conductive pads 602-3 and 602-4 are implemented and part 614-2 upon which portion 604-2 of the loop antenna is implemented. Parts 612-2 and 614-2 are separated by a fold 610-2 in flexible PCB 608-2 that positions part 612-2 approximately perpendicular to part 614-2 so as to be parallel with and to face part 612-1 as noted above.

Various parts of antenna assembly 600 housed within components 702 and 704 may be configured such that conductive pads 602 properly align to form coupling capacitors (i.e., non-galvanic couplings) when components 702 and 704 are coupled together (e.g., by way of coupling mechanism 706). Specifically, for example, when sound processor component 702 is coupled with battery component 704, conductive pads 602-1 through 602-4 may be configured to cause the first and second coupling capacitors (e.g., in combination with other capacitance along the loop antenna) to collectively resonate with an inductance of the loop antenna at a carrier frequency at which data is transferred by way of the loop antenna (e.g., a carrier frequency within the 2.4 GHz spectrum used for BLUETOOTH or another suitable frequency). To this end, conductive pads 602 may be sized, shaped, spaced, distributed, and/or otherwise configured so as to form coupling capacitors having particular capacitances when components 702 and components 704 are coupled together. However, as mentioned above, conductive pads 602 may not be interconnected by way of any galvanic connection even when sound processor component 702 and battery component 704 are coupled.

Figure 7:
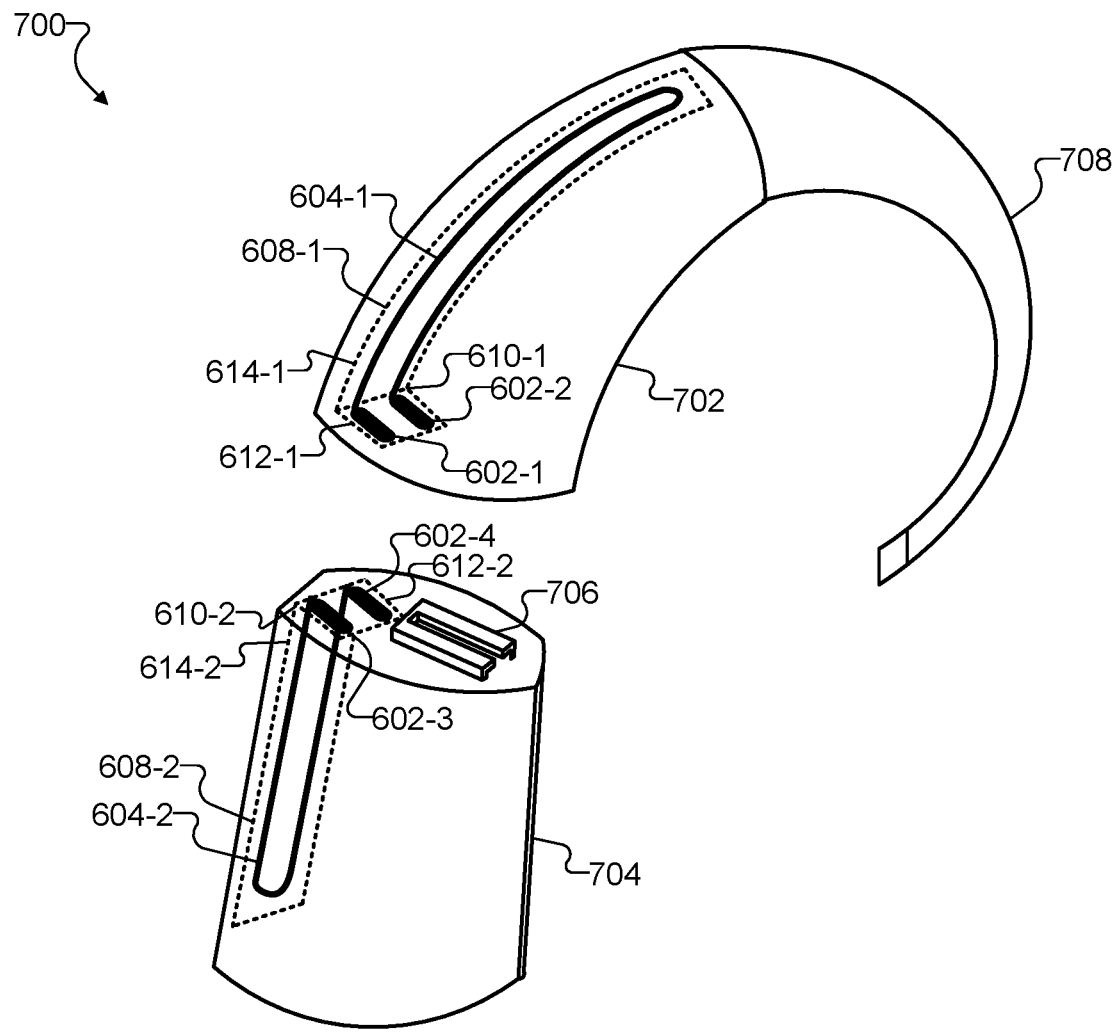
FIG. 7 illustrates a perspective view of a multi-component hearing system housing the antenna assembly of FIG. 6 according to principles described herein.

FIG. 7 illustrates how antenna assembly 600 may be housed and implemented within a sound processor component and a battery component of multi-component hearing system 700. It will be understood however, that an antenna assembly may be distributed across any of various types of multi-component systems in any of various ways according to principles described herein. For example, as mentioned above, other types of multi-component systems besides multi-component hearing systems may be used to house various portions of an antenna assembly.

Moreover, even within a multi-component hearing system such as the BTE sound processor assembly illustrated in FIG. 7, other components besides the sound processor component and the battery component may be used to house various portions of an antenna assembly. For instance, in certain loop antenna assembly implementations, the first component in which the first and second conductive pads and the first portion of the loop antenna are housed may be a sound processor component similar to sound processor component 702 (i.e., configured to process an audio signal and direct stimulation representative of the audio signal to be presented to a user of the multi-component hearing system), and the second component in which the third and fourth conductive pads and the second portion of the loop antenna are housed may be an extension unit component of the multi-component hearing system configured to augment a functionality of the sound processor component. In other words, rather than a battery component such as battery component 704, an extension unit (e.g., coupled between the sound processor component and a battery component) that augments the functionality of the multi-component hearing system in some way may be used to house at least part of the antenna assembly.

The extension unit may add any suitable functionality to the multi-component hearing system. For example, in certain implementations, the extension unit may add additional communication capabilities (e.g., the ability to transmit and/or receive signals over particular communication protocols and/or at particular frequencies) or additional programming and/or analysis capabilities for improving and catering sound processing functionality according to the needs of a specific user. In other implementations, the extension unit may add additional battery capacity (i.e., the extension unit may implement a battery pack extension), may be used primarily for the purpose of extending the antenna length (i.e., to achieve the benefits described herein), or may be used for any other suitable purpose.

To illustrate, FIG. 8A shows an exemplary configuration of how portions of an exemplary extended length loop antenna may be housed within components of an exemplary multi-component system with more than two detachable components. Specifically, using a similar numbering scheme as antenna assembly 600, an antenna assembly 800-A in FIG. 8A includes four conductive pads 802 (i.e., conductive pads 802-1 through 802-4), two portions 804 of a loop antenna (i.e., portions 804-1 and 804-2) that terminate at conductive pads 802 and further include, distributed along their length, a plurality of a discrete capacitors 806. While certain aspects of antenna assembly 800-A are not explicitly labeled, FIG. 8A shows that antenna assembly 800-A has other similarities with antenna assembly 600 such as that the portions 804 of the loop antenna are implemented on flexible PCBs having respective folds 810 (i.e., folds 810-1 and 810-2) to position respective parts of the flexible PCB that include the conductive pads 802 at an angle (e.g., at approximately a perpendicular angle) with respective parts of the flexible PCB that include the portion 804 of the loop antenna.

FIG. 8A further illustrates a multi-component system 820 that includes three components 822, 824, and 826. Multi-component system 820 may be implemented as any suitable type of multi-component system described herein, including as a multi-component hearing system performing a function similar to one or more of systems 200, 400, and/or 500 or a component included therein (e.g., one of sound processor assemblies 204, 404 or 504). As such, the components of system 820 may be implemented as any components as may serve a particular implementation. For example, if multi-component system 820 is a multi-component hearing system, any of components 822, 824, and/or 826 may be implemented as a sound processor component, an extension unit component, a battery component, an earhook component, a cable component (e.g., a cable that communicatively couples a sound processor component to a headpiece), and/or any other component as may serve a particular implementation. As one specific example, for instance, component 822 (i.e., which may house the part of antenna assembly 800-A associated with first portion 804-1) may be implemented as a sound processor component, component 824 (i.e., which may house the part of antenna assembly 800-A associated with second portion 804-2) may be implemented as an extension unit component, and component 826 (i.e., which may not house any part of antenna assembly 800-A) may be implemented as a battery unit component.

In certain examples, it may be desirable to extend a loop antenna assembly over more than two components (i.e., three or more components) of a multi-component system such as multi-component system 820. For example, by extending a loop antenna assembly over three or more components of a multi-component system, an even longer loop antenna may be formed that may efficiently transmit at frequencies at which shorter loop antennas are not able to efficiently transmit. As one exemplary implementation of such an antenna assembly, the first component in which the first and second conductive pads and the first portion of the loop antenna are housed may be a sound processor component of a multi-component hearing system (e.g., configured to process an audio signal and direct stimulation representative of the audio signal to be presented to a user of the multi-component hearing system), and the second component in which the third and fourth conductive pads and the second portion of the loop antenna are housed may comprise a plurality of subcomponents each housing at least one respective subportion of the second portion of the loop antenna. For instance, the plurality of subcomponents may include an extension unit component configured to augment a functionality of the sound processor component and a battery component configured to provide electrical power to the sound processor component. As such, each respective subportion of the second portion of the loop antenna may be capacitively coupled with other subportions of the second portion of the loop antenna by way of additional conductive pads that form additional non-galvanic couplings.

To illustrate, FIG. 8B shows an antenna assembly 800-B configured to be distributed across all three components 822, 824, and 826 of multi-component system 820. Specifically, as shown in FIG. 8B, the parts of antenna assembly 800-B associated with portion 804-1 of the loop antenna (e.g., the parts housed within a sound processor component implementing component 822) may be similar or identical as the corresponding parts of antenna assembly 800-A in FIG. 8A. However, the parts of antenna assembly 800-B associated with portion 804-2 of the loop antenna may be split into two subportions 818 (i.e., subportion 818-1, which may be housed within component 824, and subportion 818-2, which may be housed within component 826). As shown, subportions 818 may be capacitively coupled with portion 804-1 by way of non-galvanic couplings formed by conductive pads 802-1 and 802-3, and by 802-2 and 802-4 (i.e., similar to the non-galvanic couplings formed in antenna assembly 800-A). Additionally, as shown, subportions 818 may be capacitively coupled with one another by way of additional non-galvanic couplings formed by additional conductive pads 802-5 and 802-7, and by conductive pads 802-6 and 802-8. For example, these additional non-galvanic couplings may be formed in a similar way as the non-galvanic couplings formed by conductive pads 802-1 through 802-4 by using additional folds 810-3 and 810-4 in flexible PCBs associated with subportions 818-1 and 818-2, respectively. As shown, discrete capacitors 806 may be included on each of subportions 818. However, it will be understood that, since the non-galvanic couplings formed by conductive pads 802-5 through 802-8 may provide additional capacitance for three-portion antenna assembly 800-B, fewer discrete capacitors 806 may be used to resonate the loop antenna than may be used, for example, with two-portion antenna assembly 800-A.

While FIG. 8B illustrates a loop antenna divided into three components of a multi-component system, it will be understood that the loop antenna may be divided over any suitable number of components (e.g., including over more than three components) in certain implementations. Additionally, it will be understood that other types of antennas besides loop antennas (e.g., monopole antennas, bipole antennas, etc.) may similarly be implemented using the same principles described above. For example, in certain implementations, an antenna assembly may include 1) a first conductive pad housed within a first component of a multi-component system, 2) a first portion of an antenna (e.g., a loop antenna, a monopole antenna, a dipole antenna, etc.) housed within the first component and terminating on one side at the first conductive pad, 3) a second conductive pad and a third conductive pad housed within a second component of the multi-component system distinct from the first component and configured to detachably couple with the first component, 4) a second portion of the antenna housed within the second component and terminating on one side at the second conductive pad and on another side at the third conductive pad, 5) a fourth conductive pad housed within a third component of the multi-component system distinct from the first and second components and configured to detachably couple with the second component, and 6) a third portion of the antenna housed within the third component and terminating on one side at the fourth conductive pad.

When the first component and the third component are each coupled with the second component in such an antenna assembly, the first and second conductive pads may form a first coupling between the first and second portions of the antenna while the third and fourth conductive pads may form a second coupling between the second and third portions of the antenna. In some examples, these first and second couplings may be capacitive, non-galvanic couplings such as other couplings described herein. In other examples, the first and second couplings may instead by galvanic couplings that conductively couple the respective conductive pads (i.e., whereby the respective conductive pads actually contact one another so that direct current may flow between them). In still other examples, the first coupling and the second coupling may be different types of couplings. For instance, one of the couplings (e.g., the first coupling) may be a capacitive coupling while the other coupling (e.g., the second coupling) may be a galvanic coupling.

Figure 9A:
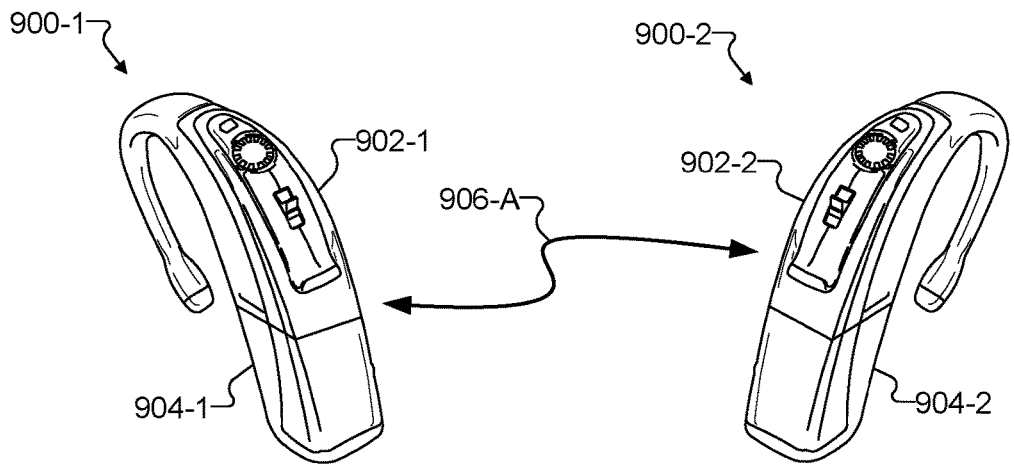
FIGS. 9A through 9C illustrate wireless communications between an exemplary multi-component system having an extended length antenna assembly and various other systems according to principles described herein.
Figure 9B:
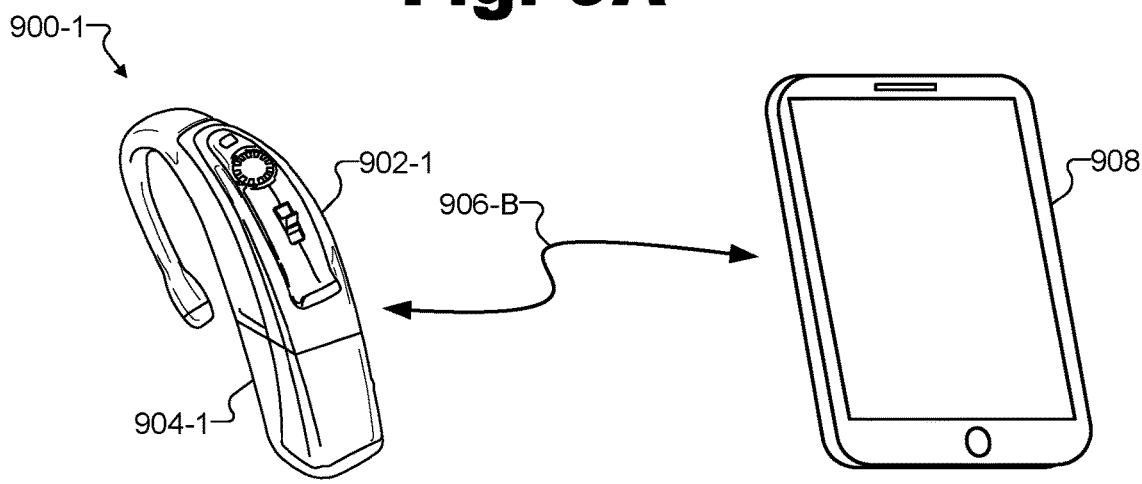
Figure 9C:
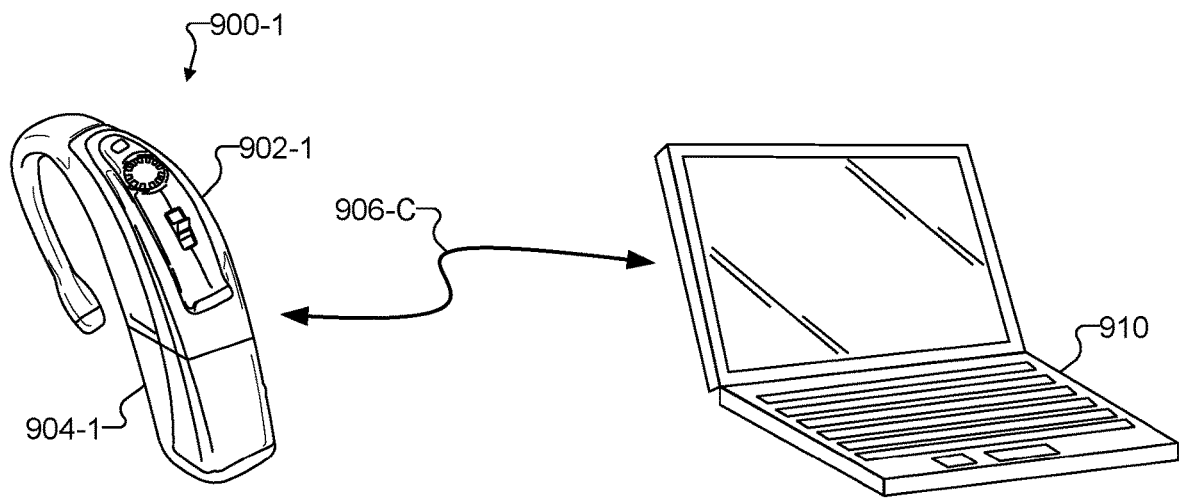

To illustrate how extended length antenna assemblies may be used within multi-component systems in operation, FIGS. 9A through 9C show wireless communications between an exemplary multi-component system having an extended length antenna assembly and various different other systems. Specifically, each of FIGS. 9A through 9C illustrates a multi-component system 900-1 implemented by a sound processor assembly of a multi-component hearing system similar to any of the sound processor assemblies described herein. As shown, multi-component system 900-1 includes a sound processor component 902-1 and a battery component 904-1 that may be similar to any of the sound processor components and/or battery components described above. While additional extension unit components are not explicitly illustrated for multi-component system 900-1, it will be understood that one or more additional components (e.g., extension unit components) may also be included with components 902-1 and 904-1 in multi-component system 900-1, and that multi-component system 900-1 may be implemented as any type of multi-component system (e.g., including other types besides multi-component hearing systems).

In FIG. 9A, multi-component system 900-1 is shown to communicate with a second multi-component system 900-2 by way of a wireless communication link 906-A, which may be implemented as, for example, a BLUETOOTH link, a Wi-Fi link, a proprietary binaural communication link, or another suitable link. Multi-component system 900-2 may be similar to multi-component system 900-1 by including, as illustrated, a sound processor component 902-2, a battery component 904-2, and the like. However, multi-component system 900-2 may be used in a binaural hearing system for a different ear of a user than multi-component system 900-1 is used for. As such, the sound processor assemblies implementing multi-component systems 900-1 and 900-2 may be worn by a user at each ear of the user and wireless communication link 906-A may transmit data between the sound processor assemblies on either side of the user's head.

Because the human head may absorb a relatively large amount of radiated energy at the frequencies used by multi-component systems 900-1 and 900-2 (e.g., BLUETOOTH frequencies in the 2.4 GHz spectrum, for example), it may be desirable for multi-component systems 900-1 and 900-2 to have relatively high radiation efficiencies so as to be able to establish and maintain wireless communication link 906-A to be reliable and efficient. As such, the principles described herein for extended length antenna assemblies may improve the performance of a binaural hearing system including multi-component systems 900-1 and 900-2 significantly.

Moreover, in certain examples, other steps may be taken to improve the reliability and efficiency of wireless communication link 906-A along with using extended length antenna assemblies within multi-component systems 900-1 and 900-2. For example, the antennas used in each of multi-component systems 900-1 and 900-2 may be configured so as to have a focused polar pattern (i.e., as opposed to an omnidirectional polar pattern) specially configured to radiate and receive energy through the head, around the back of the head, and so forth so as to radiate more energy to the other multi-component system and less energy outward to areas away from the other multi-component system. Additionally, to further improve the reliability and efficiency of wireless communication link 906-A, a loop antenna (e.g., a folded dipole antenna) may be used to lessen susceptibility to interference from the head of the user as compared to, for example, a monopole antenna. Specifically, for example, the loop antennas housed within multi-component systems 900-1 and 900-2 may each be implemented as folded dipole antennas having a total length (e.g., when the sound processor component is coupled with the battery component) that is greater than half of a wavelength corresponding to a carrier frequency at which data is transferred by way of the folded dipole antenna.

In other examples such as those illustrated in FIGS. 9B and 9C, multi-component system 900-1 may communicate with other types of systems or devices over similar wireless communication links. For example, as shown in FIG. 9B, multi-component system 900-1 may communicate with a mobile device 908 (e.g., a smartphone, a tablet device, etc.) over a wireless communication link 906-B (e.g., which may be a BLUETOOTH link or the like, similar to wireless communication link 906-A). As another example, as shown in FIG. 9C, multi-component system 900-1 may communicate with another type of computing device 910 (e.g., a laptop device, a television device, etc.) over a wireless communication link 906-C (e.g., which may also be a BLUETOOTH link or the like, similar to wireless communication links 906-A and 906-B). In certain examples, a binaural hearing system may intercommunicate between two sound processor assemblies (e.g., between multi-component systems 900-1 and 900-2 over wireless communication link 906-A) while simultaneously intercommunicating between one or both of the sound processor assemblies and another device (e.g., between one or both of multi-component systems 900-1 and 900-2 and one or both of devices 908 and 910 over one or both of wireless communication links 906-B and 906-C).

In order to communicate over wireless communication links 906-A or 906-B with multi-component system 900-1, devices 908 and 910 may include their own respective antennas. In certain examples, these antennas may also be loop antenna assemblies distributed over multiple components according to principles described herein. In other examples (e.g., where devices 908 and/or 910 include components large enough to house loop relatively large loop antennas), conventional one-portion loop antennas or other types of antennas may be employed.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A multi-component hearing system comprising:
   a sound processor component configured to process an audio signal and direct stimulation representative of the audio signal to be presented to a user of the multi-component hearing system, the sound processor component housing a first flexible printed circuit board upon which are implemented a first conductive pad, a second conductive pad, and a first portion of a loop antenna that terminates on one side at the first conductive pad and on another side at the second conductive pad; and an additional component distinct from the sound processor component and configured to detachably couple with the sound processor component, the additional component housing a second flexible printed circuit board upon which are implemented a third conductive pad, a fourth conductive pad, and a second portion of the loop antenna that terminates on one side at the third conductive pad and on another side at the fourth conductive pad;

wherein, when the sound processor component is coupled with the additional component:

the first and third conductive pads form a first non-galvanic coupling that capacitively couples the first and second portions of the loop antenna, and the second and fourth conductive pads form a second non-galvanic coupling that capacitively couples the first and second portions of the loop antenna.

2. The multi-component hearing system of claim 1, wherein the loop antenna is implemented as a folded dipole antenna having a total length, when the sound processor component is coupled with the additional component, that is greater than half of a wavelength corresponding to a carrier frequency at which data is transferred by way of the folded dipole antenna.

3. The multi-component hearing system of claim 1, further comprising one or more discrete capacitors connected in series along at least one of the first and second portions of the loop antenna and collectively configured, in combination with the first and second non-galvanic couplings, to resonate with an inductance of the loop antenna at a carrier frequency at which data is transferred by way of the loop antenna.

4. The multi-component hearing system of claim 3, wherein each of the one or more discrete capacitors connected in series along the at least one of the first and second portions of the loop antenna have a capacitance matched to a capacitance of the first non-galvanic coupling and to a capacitance of the second non-galvanic coupling.

5. The multi-component hearing system of claim 1, wherein each of the first, second, third, and fourth conductive pads are configured to cause the first and second non-galvanic coupling, in combination with other capacitance along the loop antenna and when the sound processor component is coupled with the additional component, to collectively resonate with an inductance of the loop antenna at a carrier frequency at which data is transferred by way of the loop antenna.

6. The multi-component hearing system of claim 1, implemented as a multi-component cochlear implant system in which:

the audio signal that the sound processor component is configured to process is an acoustic audio signal detected by a microphone associated with the sound processor component; and the stimulation representative of the audio signal and directed by the sound processor component to be presented to the user is electrical stimulation presented by way of a cochlear implant implanted within the user.

7. The multi-component hearing system of claim 1, implemented as at least one of:

a multi-component hearing aid system in which:

the audio signal that the sound processor component is configured to process is an acoustic audio signal detected by a microphone associated with the sound processor component, and the stimulation representative of the audio signal and directed by the sound processor component to be presented to the user is acoustic stimulation presented by way of a loudspeaker associated with an ear of the user; or a multi-component earphone system in which:

the audio signal that the sound processor component is configured to process is an electrical audio signal received by the sound processor component, and the stimulation representative of the audio signal and directed by the sound processor component to be presented to the user is acoustic stimulation presented by way of a loudspeaker associated with an ear of the user.

8. The multi-component hearing system of claim 1, wherein the first and second flexible printed circuit boards are each implemented as a foldable printed circuit board configured to be folded such that a first part of the foldable printed circuit board is at an approximately perpendicular angle to a second part of the foldable printed circuit board.

9. The multi-component hearing system of claim 8, wherein:

the first flexible printed circuit board includes a first fold forming the approximately perpendicular angle between a first part of the first flexible printed circuit board upon which the first and second conductive pads are implemented and a second part of the first flexible printed circuit board upon which the first portion of the loop antenna is implemented; and the second flexible printed circuit board includes a second fold forming the approximately perpendicular angle between a first part of the second flexible printed circuit board upon which the third and fourth conductive pads are implemented and a second part of the second flexible printed circuit board upon which the second portion of the loop antenna is implemented.

10. An antenna assembly comprising:

a first flexible printed circuit board housed within a first component of a multi-component system;

a first conductive pad and a second conductive pad implemented on the first flexible printed circuit board;

a first portion of a loop antenna implemented on the first flexible printed circuit board and terminating on one side at the first conductive pad and on another side at the second conductive pad;

a second flexible printed circuit board housed within a second component of the multi-component system distinct from the first component and configured to detachably couple with the first component;

a third conductive pad and a fourth conductive pad implemented on the second flexible printed circuit board; and a second portion of the loop antenna implemented on the second flexible printed circuit board and terminating on one side at the third conductive pad and on another side at the fourth conductive pad;

wherein, when the first component is coupled with the second component in a standard configuration:

the first and third conductive pads form a first non-galvanic coupling that capacitively couples the first and second portions of the loop antenna, and the second and fourth conductive pads form a second non-galvanic coupling that capacitively couples the first and second portions of the loop antenna.

11. The antenna assembly of claim 10, wherein the loop antenna is implemented as a folded dipole antenna having a total length, when the first component is coupled with the second component, that is greater than half of a wavelength corresponding to a carrier frequency at which data is transferred by way of the folded dipole antenna.

12. The antenna assembly of claim 10, further comprising one or more discrete capacitors connected in series along at least one of the first and second portions of the loop antenna and collectively configured, in combination with the first and second non-galvanic couplings, to resonate with an inductance of the loop antenna at a carrier frequency at which data is transferred by way of the loop antenna.

13. The antenna assembly of claim 12, wherein each of the one or more discrete capacitors connected in series along the at least one of the first and second portions of the loop antenna have a capacitance matched to a capacitance of the first non-galvanic coupling and to a capacitance of the second non-galvanic coupling.

14. The antenna assembly of claim 10, wherein each of the first, second, third, and fourth conductive pads are configured to cause the first and second non-galvanic couplings, in combination with other capacitance along the loop antenna and when the first component is coupled with the second component, to collectively resonate with an inductance of the loop antenna at a carrier frequency at which data is transferred by way of the loop antenna.

15. The antenna assembly of claim 10, wherein:
the first flexible printed circuit board includes a first fold forming an angle between a part of the first flexible printed circuit board upon which the first and second conductive pads are implemented and a part of the first flexible printed circuit board upon which the first portion of the loop antenna is implemented; and
the second flexible printed circuit board includes a second fold forming an angle between a part of the second flexible printed circuit board upon which the third and fourth conductive pads are implemented and a part of the second flexible printed circuit board upon which the second portion of the loop antenna is implemented.

16. The antenna assembly of claim 10, wherein the multi-component system is a multi-component hearing system implemented as one of a multi-component cochlear implant system, a multi-component hearing aid system, and a multi-component earphone system.

17. The antenna assembly of claim 10, wherein:
the first component in which the first and second conductive pads and the first portion of the loop antenna are housed is a sound processor component of a multi-component hearing system implementing the multi-component system, the sound processor component configured to process an audio signal and direct stimulation representative of the audio signal to be presented to a user of the multi-component hearing system; and
the second component in which the third and fourth conductive pads and the second portion of the loop antenna are housed is an extension unit component of the multi-component hearing system configured to augment a functionality of the sound processor component.

18. The antenna assembly of claim 10, wherein:
the first component in which the first and second conductive pads and the first portion of the loop antenna are housed is a sound processor component of a multi-component hearing system implementing the multi-component system, the sound processor component configured to process an audio signal and direct stimulation representative of the audio signal to be presented to a user of the multi-component hearing system;
the second component in which the third and fourth conductive pads and the second portion of the loop antenna are housed comprises a plurality of subcomponents each housing at least one respective subportion of the second portion of the loop antenna, the plurality of subcomponents including an extension unit component configured to augment a functionality of the sound processor component and a battery component configured to provide electrical power to the sound processor component; and
each respective subportion of the second portion of the loop antenna is capacitively coupled with other subportions of the second portion of the loop antenna by way of additional conductive pads that form additional non-galvanic couplings.

19. A multi-component system comprising:
a first component housing a first flexible printed circuit board upon which are implemented a first conductive pad, a second conductive pad, and a first portion of a loop antenna that terminates on one side at the first conductive pad and on another side at the second conductive pad; and
a second component distinct from the first component and configured to detachably couple with the first component, the second component housing a second flexible printed circuit board upon which are implemented a third conductive pad, a fourth conductive pad, and a second portion of the loop antenna that terminates on one side at the third conductive pad and on another side at the fourth conductive pad;
wherein, when the first component is coupled with the second component:
the first and third conductive pads form a first non-galvanic coupling that capacitively couples the first and second portions of the loop antenna, and
the second and fourth conductive pads form a second non-galvanic coupling that capacitively couples the first and second portions of the loop antenna.

20. The multi-component system of claim 19, wherein the loop antenna is implemented as a folded dipole antenna having a total length, when the first component is coupled with the second component, that is greater than half of a wavelength corresponding to a carrier frequency at which data is transferred by way of the folded dipole antenna.

21. An antenna assembly comprising:
a first flexible printed circuit board housed within a first component of a multi-component system;
a first conductive pad implemented on the first flexible printed circuit board;
a first portion of an antenna implemented on the first flexible printed circuit board and terminating on one side at the first conductive pad;
a second flexible printed circuit board housed within a second component of the multi-component system distinct from the first component and configured to detachably couple with the first component;
a second conductive pad and a third conductive pad implemented on the second flexible printed circuit board;
a second portion of the antenna implemented on the second flexible printed circuit board and terminating on one side at the second conductive pad and on another side at the third conductive pad;
a third flexible printed circuit board housed within a third component of the multi-component system distinct from the first and second components and configured to detachably couple with the second component;
a fourth conductive pad implemented on the third flexible printed circuit board; and a third portion of the antenna implemented on the third flexible printed circuit board and terminating on one side at the fourth conductive pad;

wherein, when the first component and the third component are each coupled with the second component, the first and second conductive pads form a first coupling between the first and second portions of the antenna, and the third and fourth conductive pads form a second coupling between the second and third portions of the antenna.

22. The antenna assembly of claim 21, wherein:

the first coupling is a non-galvanic coupling that capacitively couples the first and second portions of the antenna; and the second coupling is a non-galvanic coupling that capacitively couples the second and third portions of the antenna.

23. The antenna assembly of claim 21, wherein:

the first coupling is a galvanic coupling that conductively couples the first and second portions of the antenna; and the second coupling is a galvanic coupling that conductively couples the second and third portions of the antenna.

24. The antenna assembly of claim 21, wherein:

the first coupling is a non-galvanic coupling that capacitively couples the first and second portions of the antenna; and the second coupling is a galvanic coupling that conductively couples the second and third portions of the antenna.

25. The antenna assembly of claim 21, wherein the first component in which the first conductive pad and the first portion of the loop antenna are housed is a sound processor component of a multi-component hearing system implementing the multi-component system, the sound processor component configured to process an audio signal and direct stimulation representative of the audio signal to be presented to a user of the multi-component hearing system.

26. The antenna assembly of claim 21, wherein the antenna is implemented as a loop antenna.

27. The antenna assembly of claim 21, wherein the antenna is implemented as a monopole antenna.

28. The antenna assembly of claim 21, wherein the antenna is implemented as a dipole antenna.

* * * * *